US00RE38141E

(19) United States
(12) Reissued Patent
Brown

(10) Patent Number: US RE38,141 E
(45) Date of Reissued Patent: Jun. 10, 2003

(54) DRY EMOLLIENT COMPOSITIONS

(75) Inventor: James H. Brown, Gilbert, AZ (US)

(73) Assignee: International Flora Technologies Ltd., Gilbert, AZ (US)

( * ) Notice: This patent is subject to a terminal disclaimer.

(21) Appl. No.: 09/975,340

(22) Filed: Oct. 12, 2001

Related U.S. Patent Documents

Reissue of:
(64) Patent No.: 6,280,746
Issued: Aug. 28, 2001
Appl. No.: 09/010,736
Filed: Jan. 22, 1998

U.S. Applications:
(63) Continuation-in-part of application No. 08/953,132, filed on Oct. 17, 1997, now Pat. No. 5,968,530.

(51) Int. Cl.[7] ..... A61K 7/00

(52) U.S. Cl. ..... 424/401; 424/59; 424/63; 424/64; 424/502; 514/844; 514/873; 514/558

(58) Field of Search ..... 424/401, 59, 63, 424/64, 502; 514/844, 873, 558

(56) References Cited

U.S. PATENT DOCUMENTS

| | | | | | |
|---|---|---|---|---|---|
| 1,944,887 | A | * | 1/1934 | Graves | 260/106 |
| 3,740,333 | A | * | 6/1973 | Hutchinson et al. | 252/48.6 |
| 3,850,827 | A | * | 11/1974 | Zipf | 252/56 S |
| 4,031,019 | A | * | 6/1977 | Bell | 252/56 S |
| 4,152,278 | A | * | 5/1979 | Bell | 252/56 S |
| 4,264,478 | A | * | 4/1981 | Seldner | 252/522 R |
| 4,315,040 | A | * | 2/1982 | Heine et al. | 426/609 |
| 4,324,703 | A | * | 4/1982 | Seldner | 252/522 R |
| 4,329,298 | A | * | 5/1982 | Brown et al. | 260/405.6 |
| 4,437,895 | A | * | 3/1984 | Koulbanis et al. | 106/245 |
| 4,510,093 | A | * | 4/1985 | Hulsmann | 260/410.9 N |
| 4,664,914 | A | * | 5/1987 | Stillman | 424/195.1 |
| 5,013,473 | A | * | 5/1991 | Norbury et al. | 252/174.13 |
| 5,043,161 | A | * | 8/1991 | Scarpelli et al. | 424/401 |
| 5,254,331 | A | * | 10/1993 | Mausner | 424/59 |
| 5,336,692 | A | * | 8/1994 | Gans et al. | 514/772 |
| 5,607,666 | A | * | 3/1997 | Masson et al. | 424/69 |
| 5,747,007 | A | * | 5/1998 | Song et al. | 424/69 |
| 5,968,530 | A | * | 10/1999 | Arquette | 424/401 |

FOREIGN PATENT DOCUMENTS

| | | | | |
|---|---|---|---|---|
| EP | 088895 | * | 3/1982 | C07C/69/527 |
| EP | 254447 A2 | * | 7/1986 | A61K/7/00 |
| IN | 172985 | * | 1/1994 | A61K/3/933 |
| JP | 61210054 | * | 9/1986 | A61K/7/00 |
| JP | 6210009 | * | 1/1987 | A61K/7/00 |
| JP | 03220112 | * | 9/1991 | A61K/7/00 |
| WO | 90/15127 | * | 12/1990 | C11C/3/10 |
| WO | 98/46200 | * | 4/1997 | A61K/7/036 |
| WO | 99/20224 | * | 10/1997 | |

OTHER PUBLICATIONS

Brown. Jojoba. House hold Pers. Prod. Ind., Abstr. No. 216207z, Essential Oils, Ciosmetics, vol. 101, pp. 38, 40, 44, 46, 48, 1984.*

Dhanvantrai, S., et al., "Process for the preparation of an improved jojoba bodycream containng transesterfied jojoba oil and jojoba oil", XP–002109310, class A6iK 7/035, abstract, (Jan. 15, 1994).*

Nonokawa, S.Y., "Preparation Jojoba Alcohol Fatty Acid Ester Esterification Jojoba Alchol Obtain Hydrolysis jojoba Oil Stearic Acid", Database WPI, *Derwent Publications,* London, GB, XP–002109311, (Sep. 18, 1986).*

Bhatia, V.K., et al., "Synthesis of Shorter Chain Alcohol Esters of Jojoba Oil", *J. of Oil Technologists Association of India,* vol. 24, No. 1, 23–25, (01–92).*

"Confetti Dermal Essentials", United–Guardian, Inc., (1997).*

"Emulsions", In Ch. 21: Particle Phenomena and Coarse Dispersions, 310–318.*

"Fragrance Products Formulated with Pemulen Polymeric Emulsifiers", *Pemulen Polymeric Emulsifiers:* BF Goodrich Company, (1990).*

"Guide to Carrier Oils/Skin Loving Massage Oil/Timeless Skin Guide", http://kamala.com/, kamala/* .html, Kamala Perfumes, Inc.*

(List continued on next page.)

*Primary Examiner*—Thurman K. Page
*Assistant Examiner*—Lakshmi Channavajjala
(74) *Attorney, Agent, or Firm*—The Halvorson Law Firm

(57) ABSTRACT

The present invention are dry-feel emollient compositions comprising jojoba oil based esters that have use in personal care, cosmetic, cosmaceutical and pharmaceutical products. These compositions are essentially solid at room temperature, can be provided in various shapes and sizes (especially as particulates such as spheres), and can be produced from combinations of fatty alcohols, isopropyl esters and wax esters obtained from the oil contained in the seed of the jojoba plant. These new compositions also increase the range of applications for cosmetic compositions through an emollient that is more polar and hydrophilic than is found in jojoba oils. The compositions of the present invention may be obtained by a novel process of a base catalyzed alcoholysis reaction between jojoba oil and an alcohol, such as isopropyl alcohol. These components, whether exclusively jojoba esters or when combined with other carrier and vehicle components (including other emollients or binders) can form excellent carrier composition for use in the cosmetic, personal care and/or pharmaceutical field. Typical materials with which the compositions of the present invention may be blended include, but are not limited to, cosmetic oils and waxes, both natural and synthetic, (including hydrogenated or partially hydrogenated oils), silicone oils, mineral oils, long chain esters, vitamins, long chain fatty acids, cosmeceuticals, pigments, botanical extracts, esters and ethers, dimers, trimers, oligomers, and polymers, and the like. The proportions of the jojoba esters should be chosen to provide the dry-feel to the composition, which is highly desired. This will usually require a weight percent that ranges from 10% to 100% by weight of carrier material in the composition.

14 Claims, No Drawings

OTHER PUBLICATIONS

"Jojoba Oil", 42–47.*
"Rich Moisturizer with B–Carotene "Silkies"", (Oct. 1993).*
"Title/Abstract: Wax Esters", US Patent Abstracs.*
Ahluwalia, J., et al., "Unsaturated Wax Esters as Furture Raw Materials for Industrial Applications", *Int. Congr. Proc. —Chem Tech '80,* Abstr. No. 9086b, Chemical Abstracts, vol. 95, 1981, 104, (1980).*
Bhatia, V., et al., "Chemistry and Utilization of Oil of Jojoba", *J. Sci. Ind.,* Abstr. No. 123500m, Industrial Carbohydrates, vol. 94, 115, (1981).*
Brown, J., "Jojoba", *Houshold Pers. Prod. Ind.,* Abstr. No. 216207z, Essential Oils, Cosmetics, vol. 101, 1984, 38, 40, 44, 46, 48, (1984).*
Hamilton, R., et al., "Comparison of Sperm–Whale Oil an Jojoba Wax", Ch. 16 In: *Memorias de la II Conferencia International Sobre La Jojoba,* 171–186, (Feb. 1976).*
Kirk–Othmer, "Waxes: Rice–Bran Wax", *Encyclopedia of Chemical Technology,* 24, 3rd Edition, John Wiley & Sons, New York, 471, (1978).*

Moshel, H., et al., "Demonstrating Perfume Fixation".*

Norris, F., et al., "Fat Splitting, Esterification, and Interesterification", Ch. 4 In: *Bailey's Industrial Oil and Fat Products,* John Wiley & Sons, New York, 130–33, 146–59, (1982).*

Sherbrooke, W., "Jojoba: An Annotated Bibliographic Update", *Supp. to Arid Lands Resource Information Paper No. 5,* Abstracts, 19,27,59,66,73, (1978).*

Wisniak, J., *The Chemistry and Technology of Jojoba Oil,* American Oil Chemists Society: Champaign, III., Abstr. No. 95087q, Chemical Abstracts, vol. 109, 102, (1987).*

* cited by examiner

DRY EMOLLIENT COMPOSITIONS

Matter enclosed in heavy brackets [ ] appears in the original patent but forms no part of this reissue specification; matter printed in italics indicates the additions made by reissue.

This application is a continuation-in-part of application Ser. No. 08/953,132, filed Oct. 17, 1997 now issued as U.S. Pat. No. 5,968,530.

This invention relates to emollient compositions for use in cosmetic, personal care and pharmaceutical preparations. The invention particularly relates to such emollient compositions and processes for their preparation, and more particularly to jojoba ester compositions which function as a dry carrier and vehicle for the delivery of actives such as fragrances, vitamins, medications, repellents, sun screens, cosmeceuticals (materials that combine a cosmetic and therapeutic effect) and the like.

BACKGROUND OF THE INVENTION

In the field of cosmetic, personal care, and pharmaceutical products emollients are usually defined as an agent that softens or smooths the skin and which tend to reduce the roughness, cracking and irritation of the skin. This smoothing is believed to be effected by the penetration of the emollient into the surface layers of tissue, through the slight congestion induced by rubbing and massage upon application, and especially through interference with sensible and insensible water loss. The ancient Greek physician, Galen, is thought to have made one of the first emollients consisting of beeswax, spermaceti, almond oil, borax and rosewater.

Emollients tend to be bland, fatty, oleaginous substances which may be applied locally to the skin, mucous membranes, or abraded tissue. One of the benefits of emollients is their ability to exclude water-soluble irritants, air, and air-borne bacteria when a layer of emollient is present. At the present, there are numerous ingredients which function as emollients in a wide variety of products, and which ingredients may act in subtly different ways. For example, certain emollients sit on the surface of the skin and serve to impede water loss from the skin. Such ingredients are generally comprised of large molecules that form a hydrophobic barrier to help prevent water from leaving the surface of the skin. Examples of such emollients are lanolin, mineral oil, silicon derivatives and petroleum jelly.

A chief use of emollients is to provide vehicles for lipid-soluble drugs (as in balms, ointments and alcohol-based liniments). Although it has often been suggested that such emollient vehicles facilitate the transport of such drugs through the skin, it has been found that when the oil:water partition coefficient is greater than 1.0, the penetration of lipid-soluble drugs tends to be impeded. Emollient substances are commonly employed in cleansing and antiphlogistic creams and lotions. Compound ointment bases, creams, and other medical applications are also general areas of use for emollients. Amongst the more common emollient materials are castor oil, corn oil, cottonseed oil, rose water ointment, apricot kernel oil, avocado oil, grape seed oil, hazelnut oil, olive oil, sesame oil, theobroma oil, almond oil, myristyl alcohol, and recently other natural oils such as jojoba oil.

Other ingredients that have been used as emollients include a number of fatty acids derived from either plants or animal sources. Fatty acids generally comprise aliphatic hydrocarbon or other organic chains with carboxylic substituents on them, typically having between 8 and 24 carbon atoms in the chain backbone. Fatty acids are often used in creams, lotions, shaving creams, lipsticks and as pressing agents in pressed powders and blushes. Fatty acids which are used in cosmetics formulations generally include at least stearic acid, oleic acid, myristic acid and palmitic acid. Other typical fatty acids include linoleic acid, behenic acid, and other common fatty acids of the general formula $C_nH_{2n+1}COOH$.

Fatty alcohols are also used as emollients. They are said to be less sticky and less heavy than many other fatty materials, such as the fatty acids, and are frequently used to improve the viscosity and stability of lotions and creams. They also have utility in reactive hair dying and perming products. Examples of fatty alcohols which find use in the field of cosmetics and personal care products are cetyl alcohol, lauryl alcohol, stearyl alcohol and oleyl alcohol.

Additional examples of emollients are fatty esters. One of the best qualities of fatty esters is that they do not feel as oily to the touch as some other types of emollient fatty ingredients. Examples include isopropyl palmitate, isopropyl myristate and glyceryl stearate.

An important emollient is jojoba oil which is derived from the seed of the species Simmondsia chinensis. Jojoba is a seed oil with excellent skin feel. The oil is composed almost exclusively of wax esters, with little or no triglycerides present. A major portion of the production of jojoba oil is used by the cosmetic industry as an emollient in a variety of products.

The art of perfumery is an ancient skill with origins generally traced to the first Dynasty of Egypt, which was ruled by Menes sometime between 3500 and 500 BC. Sesame, almond and olive oils were used as solvents to extract the aromatics from vegetable materials and also as vehicles for delivery of the aromatics to the skin. Early Greek writers recorded the use of oils to "fix" or to retard evaporation of fragrance compounds. The early Romans showed little interest in perfumes and in fact perfumed unguents were forbidden in Rome by edict in about 188 BC. By the time Nero was Emperor in A.D. 54, the Romans had migrated into southern Italy and acquired a more intimate knowledge of the aesthetic side of life from the Greeks who occupied the area. Greeks and Romans used sesame, olive, or bean oils to extract and deliver the fragrance compounds and according to Pliny, resin and gum were added to "fix" the odor lest "it is apt to die away and disappear with the greatest rapidity if these substances are not employed." The first alcoholic perfume base appeared in 1370 and was known as "Hungry Water," a name attributed to Queen Elizabeth of Hungary who first commissioned its preparation. The use of alcoholic bases to deliver fragrance compounds to the skin became the method of choice around the world. Some Middle Eastern regions still adhere to the more traditional use of sesame or olive oils as fragrance carriers.

Modern purveyors of perfumes and perfumed cosmetics have social and legal mandates to reduce the amount of Volatile Organic Compounds (VOC's) released into the atmosphere by their products. Modem technology has also identified alcohol as an agent which dries the skin and therefore there has been a desire for "alcohol free" cosmetic and personal care products. Additional carriers and vehicles for perfumes that are acceptable to the industry and consumers are also needed.

One of the problems with typical emollients is that the emollient itself provides a wet or oily feel to the applied areas. This can lead to an uncomfortable feeling or appearance to the user, which is very important in the cosmetic and pharmacological industry. An additive for cosmetic, personal care and topical treatment (medicament) products has been marketed under the name of "Confetti"™ (with different alphanumeric identifiers as to specific ingredients, e.g., Confetti™ AL with allantion, and Confetti™ EA, MT, PA, RG and SG identifying the color of the material). This material is advertised as decorative microcapsules which contribute beneficial moisturizing and delivery of alcohol soluble ingredients to the skin. Confetti™ is advertised as having a good balance of structural integrity and rub-in characteristics, rubbing into the skin completely without any extra pressure. The Material Safety Data Sheets (MSDS) on Confetti IMproducts identifies them as containing a natural oil (e.g., coconut oil, tocopheryl acetate, retinyl palmitate), propylene glycol, synthetic beeswax, petrolatum, allantion, PVM/MA Decadiene crosspolymer and benzophenone, as well as pigments and/or dyes.

SUMMARY OF THE INVENTION

Jojoba ester compositions have been found to finction well as a dry carrier or vehicle for the application of active materials to the skin or hair of customers. These esters have been found to be useful in pure or blended forms as carriers or vehicles in the personal care, cosmetic, and/or pharmaceutical fields of use. The esters to be used may be provided with a range of properties (from the composition of the ester itself or from additives and blended materials) and can provide improved feel when used with other conventional carriers, vehicles, bases, actives and additives. Upon application and 'rubbing in' of the compositions, the jojoba ester based compositions leave the skin feeling soft (which is typical of high quality emollients), yet provide a mildly persistent coating which carriers the actives without leaving a wet or oily feel to the skin of the user.

The present invention describes a very effective dry-feel emollient composition additive for use in personal care, cosmetic and pharmaceutical products and a novel method of producing that composition. The composition is essentially solid at room temperature, can be provided in various shapes and sizes (especially as spheres), and can be produced from combinations of fatty alcohols, isopropyl esters and wax esters obtained from the oil contained in the seed of the jojoba plant (Simmondsia chinensis), jojoba oil.

These new emollient compositions preserve the excellent skin feel attributed tojojoba oil, which has long been used as an emollient. These new compositions also increase the range of applications for cosmetic compositions through an emollient that is more polar and hydrophilic than is found in jojoba oils, (which may also be referred to in the art as jojoba wax esters). The composition forms stable emulsions much more readily than does jojoba oil. The composition may also further provide excellent emolliency to normally dry cosmetic systems involving high levels of pigments, with the emollient acting as a pigment wetting agent and as an aid to a smooth and even application of the dry system. It also functions as an excipient in pressed powder.

The compositions comprising fatty alcohols, isopropyl esters and jojoba wax esters (jojoba oil) may be obtained by the base catalyzed alcoholysis reaction between jojoba oil and an alkyl alcohol. In the alcoholysis reaction, examples of the base catalyst materials include, but are not limited to metal alkoxides and especially alkali metal alkoxides, inorganic hydroxides, especially alkali metal hydroxides, and the like such as $NaOCH_3$ sodium methoxide, $NaOCH_2CH_3$ sodium ethoxide (potassium, calcium and lithium counterparts), KOH & NaOH (e.g., anhydrous alkali metal hydroxides in alcohol solution, with the alcohol of the solution being the alcohol used in the reaction).

The findamental reactions used in the practice of the present invention may be generally considered in the following manner. Starting materials could include:

I. The alcohol, $R^4$—OH (with isopropyl alcohol (IPA, HO—CH—$(CH_3)_2$) being primarily emphasized), II. Jojoba Wax Esters $R^1$—COO—$CH_2$—$R^1$, and III. Fully hydrogenated Jojoba Wax Esters $R^2$—COO—$CH_2$—$R^2$ wherein $R^4$ is an alkyl group or other aliphatic group, preferably of 1 to 12 carbon atoms, more preferably an iso-alkyl group, and most preferably an isopropyl group, $R^1$ comprises $CH_3$—$(CH_2)_7$—CH═CH—$CH_2$—$(CH_2)_x$—, and $R^2$ comprises CH3—$(C_2)_y$— wherein x is 6, 8, 10 and/or 12, and y is 16, 18, 20 and/or 22.

$R^4$ comprises $C_nH_{2n+1}$—, wherein n=1 to 12.

Typical product components from the preferred synthetic reactions used in the practice of the present invention with jojoba oil may include:

Partially saturated wax esters:

IV. $R^1$—COO—$CH_2$—$R^2$ and/or V.$R^2$—COO—$CH_2$—$R^1$.

(Where isopropyl alcohol was used) iso-propyl esters

VI. $R^1$—COO—CH—$(CH_3)_2$ [generically $R_1$—COO—$R^4$] and/or

VII. $R^2$—COO—CH—$(CH_3)_2$ [generically $R^2$—COO—$R^4$] and fatty alcohols comprising VIII. $R^2$—COO—CH—$(CH_3)_2$[generically $R^2$—COO—$R^4$] and The basic reactions which may be used in the preparation of the emollient compositions of the invention derived from jojoba oil may include at least the following procedures.

Reaction A I and IIn (catalyst)→VI, VIII and IIr. This product is referred to herein as "Floraesters-IPT" and is a liquid.

Reaction B I and IIIN (catalyst)→VII, IX and IIIr. This product is referred to herein as "Floraester-HIPJ" and is a solid.

Reaction C I, and IIn and IIIn (catalyst)→IV, V, VI, VII, VIII, IX, IIr and IIIr. This product is referred to herein as "the broad melting range emollient" and the properties of the emollient depend upon the relative amounts of IIn and IIIN.

The subscripts n and r respectively represent n=the naturally occurring distribution of wax esters and r=the randomized distribution of wax esters resulting from rearrangements which occur during the reactions. It is to be noted that mixing of the reaction products from A and B will give emollients with a wide range of melting points, but will not be identical to the reaction product of C because of the absence of IV and V.

A process for producing an emollient may comprise the steps of:

a) providing a composition comprising jojoba oil, b) adding an alcohol, e.g., having from 1 to 12 carbon atoms, to said composition, c) effecting alcoholysis on said jojoba oil mixed with said alcohol to produce an emollient, and d) effecting interesterification of remaining wax esters.

In preparing the emollient composition, refined jojoba oil (or hydrogenated jojoba oil or a mixture of the oil and hydrogenated oil) is introduced into an appropriate vessel (capable of excluding air) equipped with stirring and means of heating and cooling. The jojoba oil is first dried under vacuum at a temperature of 90 C to remove most or all moisture. The anhydrous isopropyl alcohol (or other alcohol) is then added with the amount of isopropyl used being from about 20% to about 50% by weight ofjojoba oil. The reactor is sealed and heat is applied to bring the temperature of the reaction mixture to about 70–75° C. It is important that air be excluded and that the reactor be vented through a condenser to recover any unreacted alcohol. When the temperature has reached 70–75° C., a first addition of catalyst (e.g., a catalyst for alcoholysis and interesterification such as sodium methoxide) is made. The amount added ranges from about 0.05 or from 0.1% to about 0.6% by weight of the jojoba oil with about 0.3% being preferred. After about 2 hours, a sample is taken and analyzed for the presence of the wax esters. If the wax ester content is greater than about 25% by weight, and it is desired to have a lower level of wax esters present in the reaction mixture, a second addition of catalyst is made, about 0.1% by weight of the original amount of jojoba oil. The reaction is then continued for an additional one hour. The reaction mixture is then sampled and analyzed again. If the residual wax ester content is less than about 25–35%, the reaction may be considered to be complete. Heating is discontinued but no cooling is applied. If the reaction is considered incomplete, a third catalyst addition may be made and the reaction continued as previously described. Any remaining catalyst can be neutralized and deactivated by the addition of citric acid. After about 15 minutes of agitation the neutralized catalyst (sodium citrate) is removed by filtration. Once the catalyst has been removed, any remaining isopropyl alcohol can be distilled from the product and the recovered isopropyl alcohol should be kept absolutely dry in order to be able to be used again.

As used in this description of the present invention, Floraesters 70 is III, Floraesters 15 is IIr, Floraesters 20, 30 and 60 are combinations of IIr, IV, V, and IIIr, Floraesters IPJ is a mixture of IIr, VI, and VIII, and Floraesters HIPJ is a combination of IIIr, VII and IX.

DETAILED DESCRIPTION OF THE INVENTION

Jojoba oil and its derivatives comprise a family of wax esters which have melting points which range from 10 to 71° C. At room temperature (~20° C.), this family of esters varies from pourable liquids, to soft creams, to pasty waxes, to a brittle hard wax. Jojoba esters may be used individually or can be blended with the different melting point esters within the family to form products with selected melting points and specific physical properties or feel. These esters, whether exclusively jojoba esters or when combined with other carrier and vehicle components (including other emollients or binders) can form excellent carrier and vehicle or delivery compositions for use in the cosmetic, personal care and/or pharmaceutical field, including the cosmeceutical field where cosmetic compositions also provide pharmaceutical or other therapeutic benefits. Typical materials with which the jojoba esters may be blended in accordance with the practice of the present invention include, but are not limited to, cosmetic oils and waxes, both natural and synthetic, including hydrogenated or partially hydrogenated oils, silicon oils, mineral oils, long chain esters, vitamins (especially vitamin E), long chain fatty acids, alcohols, cosmeceuticals, pigments, botanical extracts, esters and ethers, dimers, trimers, oligomers, and polymers, and the like. These blended compositions may of course be combined with the active ingredients intended to be delivered by the compositions used in the present invention. The proportions of the jojoba esters should be chosen to provide the dry-feel to the composition which is highly desired. This will usually require at least 10%, often at least 20%, preferably at least 30%, more preferably at least 40 or 50%, by weight, and most preferably at least 60, at least 70, at least 80, and at least 90% (up to 100% by weight) by weight of carrier material (excluding solvent and actives) in the composition.

The dry-feel compositions of the present invention may be applied to the skin as particulate materials, usually in a cosmetic, personal care, cosmeceutical or pharmaceutical composition. The processes of making the particles generally provides them as spherical or oblong particles, but they may be shaped by pressing, molding, spray drying, atomization or other stresses to provide shaped particles, including platelets. The jojoba esters have particular properties which renders them especially suitable for use in fragrance dispensing compositions and topical applications, and those properties include their spreadability, emolliency, non-volatility, lack of color and lack of odor. The lack of odor is mildly important in pharmaceutical applications, but is viewed as particularly essential in the provision of fragrances. Perfume and cosmetic providers have extremely rigid standards on non-essential odor contribution in their products.

By skillful blending, a mixture ofjojoba esters with fragrance oils can be prepared that melt at slightly below skin temperature. When formed into spherical particles and rubbed into the skin, these spherical particles disappear into the skin. Indeed they soften, melt and are adsorbed onto the surface of the skin where they deposit a layer of the jojoba esters containing fragrance. Jojoba esters are non-volatile and form an imperceptible film on the skin that slows down the release of the fragrance. These jojoba esters, being low in odor and superior skin emollients, provide an excellent carrier and delivery system for fine fragrances.

Spheres formed from the present invention which contain fragrance or perfume can be incorporated into a larger variety of cosmetic and personal care products for the purpose of providing emolliency to the skin. At the same time, these fragrances bearing spheres serve to deliver fragrance oils to the skin. Traditional methods of fragrance delivery utilize fragrance oils incorporated in alcohol, typically ethyl alcohol. These traditional carriers of fragrance oils are, by definition Volatile Organic Compounds (VOC's) which evaporate into the air after being applied to the skin. The present invention provides a method to deliver fragrance oils to the skin and minimize VOC emissions.

Jojoba (Simmondsia chinensis) is a New World crop recently domesticated and now cultivated around the world in regions with a climate similar to the Sonora Desert of Arizona and northern Mexico where jojoba originated. Jojoba oil is extracted from the seed of the female jojoba bush. The oil is found in the seed at levels normally exceeding 50% by weight but usually less than 55%. This "oil" is not a triglyceride such as sesame or almond oils, but is instead a long chain ester, typically 42 carbons in length and composed of monounsaturated fatty acids combined with monounsaturated fatty alcohols. The viscosity and appearance ofjojoba oil are not unlike triglyceride oils although the tactile properties ofjojoba oil render it an excellent "non oily" skin emollient. Jojoba has an unusual affinity for the skin. Unlike sesame oil or almond oil, jojoba oil is unusually resistant to oxidative degradation and rancidity. Jesuit missionaries in the southwestern USA and northern Mexico recorded the use of jojoba oil by the indigenous people of the area as a treatment for wounds and as a hair preparation.

Jojoba esters are prepared by processes described herein, which processes result in a randomized molecular combination of saturated with unsaturated jojoba fatty acids and fatty alcohols. These esters are a complex mixture of different jojoba fatty acids and fatty alcohols combined randomly and composed of differing chain lengths. The fatty acids and fatty alcohols may be either fully saturated, monounsaturated or with both the fatty alcohol and the fatty acid containing one point of unsaturation, as described above. The melting point, consistency, and physical appearance of these jojoba esters can be manipulated to produce a family of wax esters ranging from pourable liquids to hard, crystalline waxes.

Jojoba esters are excellent carriers of fragrance oil. As fragrance oil carriers they are not prone to the development of rancidity or other unpleasant odors, resulting in delivery of the fragrance compound to consumers in a form as near that created by the perfumer as possible. The physical form of the jojoba ester and fragrance oil system can be adjusted to accommodate any type of consumer product application desired. As an example, fragrance oils can be incorporated in liquid, pourable jojoba esters that at ambient temperatures can be used by a consumer in a manner similar to the traditional use of alcohol and fragrance oil blends. Jojoba esters containing fragrance oil can be formed into spheres and these spheres subsequently incorporated into cosmetic bases with a wide range of physical and chemical properties. In this spherical form (as a discontinuous phase or dispersed phase), the jojoba esters serve to minimize the level of contact of the fragrance oil with the cosmetic base (as a continuous phase). This is a desirable effect when the fragrance oil contains components that are not compatible with the cosmetic base, or vice versa. The particles are usually present as a dispersion of the particles in a flowable continuous phase carrying medium which is not a solvent for said particles. By flowable, it is meant that the carrying medium may be a liquid, higher viscosity fluid (such as a gel) or other material which can be spread by manual pressure in applications to the skin. The aspect of non-dissolvability of the particles within the carrying medium is desirable so that the particles do not dissolve into the carrying medium and destroy the dispersed nature of the combination. The combination may use a solvent carrier for the esters, if it is acceptable in the particular use to have the particles dissolved and the ester carried as a solute.

Cosmetic pancake carrying media are poured products that are permitted to solidify into a cake and is applied with the fingertips or with an applicator such as a cosmetic sponge. In mixing the formulas for cosmetic pancake carrying media, waxes are melted at approximately 72 degrees Celsius and mixed with isopropyl myristate at the same temperature, thereby creating a heated ointment. The dry powders are pulverized several times until fully mixed. The dry powders are then added to the heated ointment. This mixture is then passed through either a colloid, ointment, or roller mill. Finally the mixture is agitated at a slow rate and permitted to cool to about 45 degrees Celsius; perfume and micro particles such as the emollient spheres according to the present invention are added and poured into containers. The mixture is then slowly cooled as cooling the mixture too rapidly will cause the cake to crack. The viscosity of the resulting product is low thereby making it easier to eliminate entrapped air. The formula for cosmetic pancake carrying media, as it relates to the present invention, includes micro particles ranging from 0.10% to 20.0%, preferably though, 1.0% by weight of the formulation, depending upon the requirements of the final application.

Individual jojoba esters or blends of the esters can be warmed to just above their melting point, a fragrance oil incorporated, and then the molten blend poured into a jar or other dispersing package where it will solidify upon cooling. The consistency of the blended product in the container can be adjusted to facilitate its application to the skin by use of the fmgers or by a method of application using the packaging material.

Fragrance oils are normally compounded to exhibit a range of natural volatility. Jojoba esters finction as "fixatives" which help control the premature release of volatile components of fragrance oils. This "fixative" function ofjojoba esters can be manipulated for optimum compatibility with different fragrance oils by skiliftil blending ofjojoba esters of different melting points, without the jojoba oil reacting with the fragrance oil. Jojoba esters in the present invention are utilized as oxidatively stable carriers of fragrance oils and are capable of being modified or blended in different ratios to arrive at the optimum "skin feel" and "fixative" fuinction that might be desired.

The emolliency of jojoba is well known to those skilled in the art of cosmetic formulation. When applied to the skin, jojoba esters function as emollients to preserve and retain the natural moisture levels in the skin. Unlike volatile alcohols, jojoba esters are non-drying and in fact soften and moisturize the skin. The use of these jojoba esters as carriers for delivery of fragrance oils results in lower VOC emissions, a fixative effect for the fragrance oils, and also results in enhancing the moisture level of skin to which the jojoba esters are applied. When botanical extracts are incorporated with the jojoba esters, the esters also serve to disperse the botanicals evenly over the skin.

TYPICAL PROPERTIES OF JOJOBA ESTERS:

| | Melting Point | Iodine Value |
|---|---|---|
| Floraesters - 70 | 66–70° C. | <2 |
| Floraesters - 60 | 56–60° C. | 40–44 |
| Floraesters - 30 | 47–51° C. | 57–61 |
| Floraesters - 20 | 42–48° C. | 64–70 |
| Floraesters - 15 | 10–15° C. | 78–85 |
| Floraesters IPJ | 6–12° C. | 75–85 |
| Floraesters HIPJ | 55–65° C. | <2 |

EXAMPLES

Formula 1.

| | |
|---|---|
| Floraesters - 60 | 90 grams |
| Fragrance Oil | 10 grams |

This blend of Jojoba Esters and fragrance oil melts at approximately skin temperature and if desired, can be formed into small spheres for direct application to the skin or for incorporation in other cosmetic base formulas.

| Formula 2. | |
|---|---|
| Floraesters - 15 | 60 grams |
| Fragrance Oil | 40 grams |

This blend of Jojoba Esters and fragrance oil is liquid at ambient temperature and be applied to the skin in the manner of traditional perfumes.

| Formula 3. | |
|---|---|
| Floraesters - 60 | 75 grams |
| Floraesters - 70 | 10 grams |
| Fragrance Oil | 35 grams |

This blend of two Jojoba Esters plus fragrance oil melts at just above skin temperature and is suitable for direct application to the skin or can first be formed into spheres for subsequent incorporation in other cosmetic bases.

| Formula 4. | |
|---|---|
| Floraesters - IPJ | 25 grams |
| Floraesters - 20 | 10 grams |
| Floraesters - 30 | 10 grams |
| Fragrance Oil | 55 grams |

This blend of three Jojoba Esters with fragrance oil has the consistency of a free flowing semi-solid paste. Application of stronger levels of fragrance which are long lasting on the skin are possible utilizing this carrier system.

| Formula 5. | |
|---|---|
| Floraesters 60 | 70 grams |
| Floraesters 30 | 5 grams |
| Floraesters 70 | 15 grams |
| Fragrance Oil | 9 grams |
| FD&C Red #40 | 1 gram |

This blend of three Jojoba Esters with fragrance oils is a non-flowing semi-solid which is appropriate for direct application to the skin. A pigment has been added to increase the visual impact of the invention.

| Formula 6. | |
|---|---|
| Floraesters 60 | 72 grams |
| Floraesters 70 | 16 grams |
| Fragrance Oil | 10 grams |
| Ultramarine Blue | 2 grams |

This blend of two Jojoba Esters with fragrance oil includes a pigment selected for stability in high pH (greater than 8.0) aqueous cosmetic bases. This blend is suitable for formation into spheres and subsequent incorporation in cosmetic bases such as shower gels, facial creams, eye creams, body lotions, etc. The pigment has been selected for its compatibility with aqueous cosmetic bases.

Other compatible cosmetic ingredients may be added to any of the above formulas to achieve different melting points, flow characteristics, water resistance, etc. Examples of other cosmetic ingredients which may be suitable for addition to the above formulas are beeswax, castor wax, carnauba wax, vegetable oils, partially hydrogenated vegetable oils, surfactants such as Tween 60™ or Tween 80™, silicone preparations, fatty alcohols, fatty acids and fatty acid esters, alpha and beta hydroxy acids, vitamins (such as vitamin E, vitamin E acetate, vitamin A palmitate, beta caratene, vitamin C, etc.), herbal extracts, alpha-bisabolol, conjugated linolenic acid (CLA) antioxidants such as tocopherols or mixed natural tocopherols, other antioxidants such as BHA or BHT. Pigments may also be added to any of the above to create unique visual effects. For example:

| Formula 7. | |
|---|---|
| Floraesters 60 | 72 grams |
| Floraesters 70 | 8 grams |
| Carnauba Wax | 8 grams |
| Fragrance Oil | 10 grams |
| Red D&C #30 | 2 grams |

When formed into spheres and incorporated into low pH cosmetic bases such as cosmetic pancake, this blend of Jojoba Esters, carnauba wax, fragrance oil and pigment exhibits a resistance to softening and deterioration. Inclusion of the carnauba wax results in an even more dry feeling on the skin. This formula would be more appropriate as a fragrance delivery for individuals with oily skin.

SKIN MOISTURE DETERMINATIONS

The NOVA meter is an instrument designed to measure skin moisture. During a period of one week the instrument was used to determine a baseline moisture reading for an area of skin on the forearm approximately 4 inches above the wrist. Readings taken during the one-week period established the baseline at a reading of 101 units (as measured, for example, by a NOVA DPM 9003 instrument, which measures impedance or the capacitive reactance of the skin, cf The NOVA™ Technology Corporation Newsletter, Summer 1997) for the panelists. A higher reading indicates a more moist skin, a lower reading indicates a drier skin. The area of skin to be tested was divided laterally and marked with a pen to delineate the two skin testing areas. A 30% solution of fragrance oil (Shaw Mudge M-7108) in ethanol was prepared for application to one of the skin test areas. Formula 3 in the preceding examples was prepared for application to the other skin test area. NOVA meter readings were taken in each test area 10 minutes after application of the test materials, 30 minutes after application, one hour and three hours after application. Readings were taken in triplicate and the average taken and recorded as the result below:

| | NOVA meter reading | |
|---|---|---|
| | Alcoholic fragrance treated | Jojoba Ester treated Composition No. 3 |
| Baseline during one week | 101 | 101 |
| Ten minutes after application | 96 | 104 |
| Thirty minutes after application | 96 | 108 |
| One hour after application | 98 | 114 |
| Three hours after application | 98 | 106 |

Where the solvent effects of the ethanol in the alcoholic fragrance treated skin caused a decrease in the moisture content of the treated area, the jojoba ester treated skin exhibited an increase in skin moisture.

These and other aspects of the invention will be further described and enabled in the practice of the following, non-limiting examples.

EXAMPLES

Example 1

A moisturizer composition, in the form of the dry-feel emollient composition of the present invention in spherical particle form, was prepared as follows. The following distinct phases or compositions were used in the preparation.

| | | |
|---|---|---|
| | Deionized water | 57.85 |
| | Disodium ethylenediaminetetraacetic acid | 00.03 |
| | Carbopol ™ 981 (Carbomer, B. F. Goodrich) | 00.25 |
| A1. | Glycerine 96% (Dow) | 05.00 |
| | Polyglycol 1450 (PEG) (Dow) | 03.50 |
| | Sorbitol 70 | 03.00 |
| | Methylparaben (USP) | 00.20 |
| | Germall 115 (Imidazolidinyl urea, Sutton) | 00.10 |
| | Sodium Dehydroacetate | 00.05 |
| B. | Deionized water | 05.00 |
| | Triethanolamine | 00.70 |
| C. | Florasun 90 (Hybrid sunflower seed oil) | 05.00 |
| | Floraesters 30 (jojoba ester) | 03.10 |
| | Softisan 100 (hydrogenated coco-glycerides, Huls) | 02.00 |
| | Jojoba oil (refined grade, International Flora Technologies) | 03.00 |
| | Lexemul 561 (glyceryl stearate and PEG- 100 stearate Inolex ™) | 02.50 |
| | Shea Butter (Tri-K) | 01.50 |
| | SF-1256 Fluid (Cyclomethicone, GE) | 01.50 |
| | Pristerene 4911 (stearic acid, unichema) | 02.20 |
| | Vitamin E acetate (tocopheryl acetate, Roche) | 00.20 |
| | Propylparaben, USP | 00.10 |
| D. | Vitamin A palmitate with vitamin B-3 (Roche) | 00.02 |
| | Fragrance, (Shaw Mudge M-7323) | 00.20 |
| E. | Particulate emollients with 5% by weight B-carotene | 03.00 |

The water of phase A was heated to 800° C. Using high speed propeller agitation, the Carbopol 981 was sprinkled into the A phase. Once all of the Carbomer has been wetted out, mixing was continued for 15–20 minutes at 75° C. The remaining ingredients of phase A were then added. The ingredients of phase A1 were combined and then added to phase A. The ingredients of phase B were combined and then added to the combined phases A and A1. With medium propeller agitation. Phase C was heated to 75° C. with medium propeller stirring then added to the combined phases A, A1 and B with medium propeller stirring at 75° C. for 15 to 20 minutes. The mixture was cooled to 45° C. with stirring. Phase D was added to the blended phase A, B and C with medium propeller stirring for 15–20 minutes until the mixture appeared to be uniform. The batch was cooled to 30° C. and phase E was blended in with slow sweep agitation until the mixture appeared to be uniform.

Example 2

An aqueous gel system of suspended solid emollient particles according to the present invention was prepared as follows. The following distinct phases or compositions were used in the preparation.

| | | |
|---|---|---|
| | Deionized water | 90.29 |
| | Disodium ethylenediaminetetracetic acid | 00.03 |
| | Carbopol ™ 981 (Carbomer, B. F. Goodrich) | 00.50 |

-continued

| | | |
|---|---|---|
| B. | Propylene glycol, USP | 03.00 |
| | Propylparaben, USP | 00.05 |
| | Methylparaben (USP) | 00.25 |
| | Germall 115 (Imidazolidinyl urea, Sutton) | 00.25 |
| | Sodium Dehydroacetate | 00.03 |
| C. | Jojoba Wax PEG-120 esters | 00.30 |
| | dl-Panthenol | 00.50 |
| | Lubrajel ™ MS (polyglycolmethacrylate, Guardian) | 01.00 |
| D. | Triethanolamine | 00.80 |
| E. | Particulate emollients with 5% by weight Vitamin E acetate | 03.00 |

The Carbopol was dispersed into the water of phase A with high speed propeller mixing and heated to 70° C. The EDTA was added with propeller agitation until dissolved. The ingredients of phase B were added into phase A while mixing at 65–70° C. Phase C was added into this resulting mixture with moderate propeller agitation. The batch was force cooled, and then with moderate sweep agitation, phase D was added to the batch. pH adjustment to between about 6.8–7.2 was useful. The particulate emollient system of the invention was blended in with sweep agitation.

This example could be repeated easily with the Vitamin E acetate replaced with corresponding amounts of botanicals or other additives such as Vitamin C, calendula, ginko balboa, and the like.

What is claimed:

1. A dry composition comprising solid particles of jojoba esters and fatty alcohols carrying an active ingredient selected from the group consisting of fragrances, vitamins, medicaments, botanical exracts, ultraviolet radiation absorbers, cosmeceuticals, glitter, high loads of pigment for color delivery to skin, spices, spice extracts, herbs, and herb extracts, wherein said jojoba esters and fatty alcohols comprise at least 10% by weight of said particles and further comprise:

a. a partially saturated jojoba wax ester selected from the group consisting of at least one of the general formulae $R^1—COO—CH_2—R^2$ or $R^2—COO—CH_2—R^1$, b. an alkyl ester selected from the group consisting of at least one of the general formulae $R^1—COO—R^4$ or $R^2—COO—R^4$ and c. a fatty alcohol selected from the group consisting of at least one of the general formulae $R^1—CH_2—OH$ or $R^2CH_2—OH$, d. or various combinations thereof, wherein $R^4$ comprises $C_nH_{2n+1}$; n=1 to 12

$R^1$ comprises $CH_3—(CH_2)_7—CH{=}CH—CH_2(CH_2)_x—$, and $R^2$ comprises $CH_3—(CH_2)_y—$ wherein x is 6, 8, 10 and/or 12, and y is 16, 18, 20 and/or 22.

2. The composition of claim 1 wherein said particles comprise dyed or pigmented jojoba esters and fatty alcohols, but not an aqueous phase, carrying an active ingredient selected from the group consisting of fragrances, vitamins, medicaments, botanical extracts, ultraviolet radiation absorbers, cosmeceuticals, glitter, high loads of pigment for color delivery to skin, spices, spice extracts, herbs, and herb extracts.

3. The composition of claim 2 wherein $R^4$ comprises an iso-propyl group.

4. The composition of claim 1 wherein said jojoba esters and fatty alcohols comprise at least 11% by weight of said particles.

5. The composition of claim 4 wherein $R^4$ comprises an iso-propyl group.

6. The composition of claim 1 wherein said solid particles comprise spheres.

7. The composition of claim 2 wherein said solid particles comprise spheres.

8. The composition of claim 1 wherein said solid particles comprise spheres comprising solid particles of jojoba esters and fatty alcohols carrying at least one active ingredient selected from the group consisting of fragrances, vitamins, medicaments, botanical extracts, cosmeceuticals, ultraviolet radiation absorbers, glitter, high levels of pigment for color delivery to skin, spices, spice extracts, herbs, and herb extracts.

9. The composition of claim 1 wherein the double bond in R1 has substantially, or greater than 99.5%, only a cis configuration.

10. The composition of claim 2 wherein the double bond in R1 has substantially, or greater than 99.5%, only a cis configuration.

11. The composition of claim 9 wherein said solid particles comprise spheres.

12. The composition of claim 10 wherein said solid particles comprise spheres.

13. The composition of claim 11 wherein $R^4$ comprises an iso-propyl group.

14. The composition of claim 12 wherein $R^4$ comprises an iso-propyl group.

* * * * *

UNITED STATES PATENT AND TRADEMARK OFFICE

CERTIFICATE OF CORRECTION

PATENT NO. : RE 38,141
DATED : January 22, 1998
INVENTOR(S) : Brown

It is certified that error appears in the above-identified patent and that said Letters Patent is hereby corrected as shown below:

Title page,
Item [75], please add the name -- James S. Brown -- as a listed inventor.

Signed and Sealed this

Twenty-third Day of September, 2003

JAMES E. ROGAN
*Director of the United States Patent and Trademark Office*

UNITED STATES PATENT AND TRADEMARK OFFICE

CERTIFICATE OF CORRECTION

PATENT NO. : RE 38,141 E
DATED : June 10, 2003
INVENTOR(S) : Brown

It is certified that error appears in the above-identified patent and that said Letters Patent is hereby corrected as shown below:

Title page,
Item [75], please add the name -- James S. Brown -- as a listed inventor.

This certificate supersedes Certificate of Correction issued September 23, 2003.

Signed and Sealed this

Twenty-fifth Day of May, 2004

JON W. DUDAS
*Acting Director of the United States Patent and Trademark Office*

UNITED STATES PATENT AND TRADEMARK OFFICE

CERTIFICATE OF CORRECTION

PATENT NO. : RE38,141 E
APPLICATION NO. : 09/975340
DATED : June 10, 2003
INVENTOR(S) : Brown et al.

It is certified that error appears in the above-identified patent and that said Letters Patent is hereby corrected as shown below:

Title Page, below Item (54), should read

--(75) Inventors: James H. Brown, Gilbert, AZ (US); Demetrios James G. Arquette, Tempe, AZ (US); John Reinhardt, Riverside, CA (US)--.

This certificate supersedes the Certificates of Correction issued September 23, 2003 and May 25, 2004.

Signed and Sealed this
Third Day of April, 2012

David J. Kappos

David J. Kappos
*Director of the United States Patent and Trademark Office*

UNITED STATES PATENT AND TRADEMARK OFFICE

CERTIFICATE OF CORRECTION

PATENT NO. : RE38,141 E
APPLICATION NO. : 09/975340
DATED : June 10, 2003
INVENTOR(S) : Brown et al.

It is certified that error appears in the above-identified patent and that said Letters Patent is hereby corrected as shown below:

Title Page, below Item (54), should read

--(75) Inventors: James H. Brown, Scottsdale, AZ (US); Demetrios James G. Arquette, Tempe, AZ (US); James S. Brown, Gilbert, AZ (US); John Reinhardt, Riverside, CA (US)--.

This certificate supersedes the Certificates of Correction issued September 23, 2003, May 25, 2004, and April 3, 2012.

Signed and Sealed this
Thirteenth Day of November, 2012

David J. Kappos

David J. Kappos
*Director of the United States Patent and Trademark Office*